US009387477B2

(12) United States Patent
Ono et al.

(10) Patent No.: US 9,387,477 B2
(45) Date of Patent: Jul. 12, 2016

(54) FLUID HANDLING DEVICE

(71) Applicant: Enplas Corporation, Saitama (JP)

(72) Inventors: Koichi Ono, Saitama (JP); Ken Kitamoto, Saitama (JP)

(73) Assignee: Enplas Corporation, Saitama (JP)

( * ) Notice: Subject to any disclaimer, the term of this patent is extended or adjusted under 35 U.S.C. 154(b) by 0 days.

(21) Appl. No.: 14/731,491

(22) Filed: Jun. 5, 2015

(65) Prior Publication Data

US 2015/0360223 A1 Dec. 17, 2015

(30) Foreign Application Priority Data

Jun. 16, 2014 (JP) ................................. 2014-123551

(51) Int. Cl.

*B01L 3/00* (2006.01)
*G01N 15/06* (2006.01)
*G01N 33/00* (2006.01)
*G01N 33/48* (2006.01)

(52) U.S. Cl.

CPC ..... *B01L 3/502715* (2013.01); *B01L 3/502707* (2013.01); *B01L 2200/0689* (2013.01); *B01L 2200/12* (2013.01); *B01L 2300/0645* (2013.01); *B01L 2300/0816* (2013.01); *B01L 2300/0887* (2013.01); *B01L 2300/123* (2013.01); *B01L 2300/16* (2013.01); *B01L 2300/18* (2013.01); *B01L 2300/1827* (2013.01); *B01L 2400/0406* (2013.01)

(58) Field of Classification Search

CPC ....... G01N 15/06; G01N 33/00; G01N 33/48; B01L 3/00

USPC .......... 422/50, 68.1, 502, 503, 504, 551, 552, 422/553, 554, 547; 436/43, 180

See application file for complete search history.

(56) References Cited

U.S. PATENT DOCUMENTS

| | | | | |
|---|---|---|---|---|
| 6,939,451 | B2 | 9/2005 | Zhao et al. | |
| 7,005,179 | B2 * | 2/2006 | Davidson et al. | 428/209 |
| 7,226,564 | B2 * | 6/2007 | Ono | 422/551 |
| 7,338,637 | B2 * | 3/2008 | Pease et al. | 422/68.1 |
| 7,347,617 | B2 * | 3/2008 | Pugia et al. | 366/341 |
| 7,391,020 | B2 * | 6/2008 | Bousse et al. | 250/288 |
| 8,182,747 | B2 * | 5/2012 | Marquant et al. | 422/82.02 |
| 8,404,100 | B2 * | 3/2013 | Wu | 205/777.5 |
| 8,425,757 | B2 * | 4/2013 | Wu et al. | 205/792 |
| 8,715,475 | B2 * | 5/2014 | Plecis | 204/454 |
| 9,101,934 | B2 * | 8/2015 | Kitamoto | |

(Continued)

OTHER PUBLICATIONS

Extended European Search Report for EP 15171264.3 dated Oct. 12, 2015.

*Primary Examiner* — Brian J Sines

(74) *Attorney, Agent, or Firm* — Brundidge & Stanger, P.C.

(57) ABSTRACT

A fluid handling device includes a substrate, a film and a conductive layer. The substrate includes a through hole or a recess. The film includes first, second and third regions. The conductive layer is disposed on one surface of the film across the first, second and third regions. The first region of the film is bonded to one surface of the substrate such that one of openings of the through hole or an opening of the recess is closed to form a housing part, and that a part of the conductive layer is exposed to the inside of the housing part. The second region of the film is bent such that the conductive layer is located on an outside. The third region of the film is bonded to the first region of the film such that the conductive layer is exposed to the exterior.

8 Claims, 8 Drawing Sheets

(56) References Cited

U.S. PATENT DOCUMENTS

| | | | |
|---|---|---|---|
| 2002/0079219 | A1 | 6/2002 | Zhao et al. |
| 2012/0190591 | A1 | 7/2012 | Wohlstadter et al. |

* cited by examiner

FLUID HANDLING DEVICE

CROSS REFERENCE TO RELATED APPLICATIONS

This application is entitled to and claims the benefit of Japanese Patent Application No. 2014-123551, filed on Jun. 16, 2014, the disclosure of which including the specification, drawings and abstract is incorporated herein by reference in its entirety.

TECHNICAL FIELD

The present invention relates to a fluid handling device used for analysis and processing of a liquid sample.

BACKGROUND ART

In recent years, in the medical field or the scientific field of biochemistry, analytical chemistry and the like, micro analysis systems have been used to analyze a trace substance such as protein and nucleic acid (for example, DNA) with high accuracy and high speed. Micro analysis systems have the advantage of allowing for analysis with a very small amount of reagent or sample, and are expected to be used for various uses such as laboratory tests, food tests, and environment tests.

An example of micro analysis systems is a system that uses a microchannel chip having a minute channel to analyze a liquid sample (see, for example, PTL 1).

FIG. 1A is a plan view of microchannel chip 10 disclosed in PTL 1, and FIG. 1B is a sectional view taken along line B-B of FIG. 1A. As illustrated in FIG. 1A, microchannel chip 10 includes substrate 18 having a groove and four through holes, and plate 20 made of glass, resin, or the like provided with four electrically conductive layers (hereinafter also referred to as "conductive layer") 28 on one surface thereof. Two of the four through holes are in communication with both ends of the groove. The opening of the groove is closed with plate 20, whereby micro channel (channel) 14 is formed. In addition, the openings of four through holes on the side of the opening of the groove are closed with plate 20, whereby reservoirs 26 are formed. Plate 20 has an area larger than that of substrate 18. Each electrically conductive layer 28 is disposed on plate 20 such that one end thereof is exposed to the inside of reservoir 26, and the other end thereof is exposed to the exterior on the outside relative to the external edge of substrate 18.

The other end of electrically conductive layer 28 of microchannel chip 10 that is exposed to the exterior is connected with a measurement device and the like through a connector not illustrated. Microchannel chip 10 can be used for various types of analysis, processing, and the like of a liquid sample.

CITATION LIST

Patent Literature

PTL 1
U.S. Pat. No. 6,939,451

SUMMARY OF INVENTION

Technical Problem

In microchannel chip 10 disclosed in PTL 1, the other end of electrically conductive layer 28 configured to be connected to a connector is disposed on plate 20 having a sufficient strength at a position on the outside relative to the external edge of substrate 18. Thus, when the connector is pressed against electrically conductive layer 28, electrically conductive layer 28 can be connected to a connector with a sufficient contact pressure. Meanwhile, from the standpoint of downsizing and reduction in manufacturing cost, a film may be desired to be used in place of plate 20. In this case, disadvantageously, the film is deformed when a connector is connected to electrically conductive layer 28, and as a result, sufficient contact pressure between the connector and electrically conductive layer 28 cannot be achieved.

An object of the present invention is to provide a fluid handling device that can be manufactured by bonding a film provided with a conductive layer on one surface thereof on a substrate in which a through hole or a recess is formed, and that can be connected to a connector of a measurement device or the like with a sufficient contact pressure even when the connector is pressed against the conductive layer on the film.

Solution to Problem

To achieve the above-mentioned object, a fluid handling device according to embodiments of the present invention includes: a substrate including a through hole or a recess; a film including a first region, a second region adjacent to the first region and a third region adjacent to the second region; and a conductive layer disposed on one surface of the film across the first region, the second region and the third region, the conductive layer being configured to conduct electricity or heat. The first region of the film is bonded to one surface of the substrate such that one of openings of the through hole or an opening of the recess is closed to form a housing part for housing liquid, and that a part of the conductive layer is exposed to an inside of the housing part, the second region of the film is bent such that the conductive layer is located on an outside, and the third region of the film is bonded to the first region of the film such that the conductive layer is exposed to an exterior.

Advantageous Effects of Invention

According to the present invention, it is possible to provide a fluid handling device that can be manufactured by bonding a film provided with a conductive layer on one surface thereof on a substrate in which a through hole or a recess is formed, and that can be connected to a connector of a measurement device or the like with a sufficient contact pressure even when the connector is pressed against the conductive layer on the film. Therefore, the fluid handling device according to the embodiments of the present invention can be appropriately disposed to, for example, a measurement device having an insertion-type connector and the like, whereby measurement, processing and the like of a trace substance can be correctly performed.

DESCRIPTION OF EMBODIMENTS

In the following, embodiments of the present invention will be described in detail with reference to the accompanying drawings. In the following description, as typical examples of a fluid handling device according to the embodiments of the present invention, a microchip and a microchannel chip will be described.

Embodiment 1

In Embodiment 1, microchip 100 that can perform heat treatment of liquid such as reagent and a liquid sample is described.

(Configuration of Microchip)

Figure 2A:
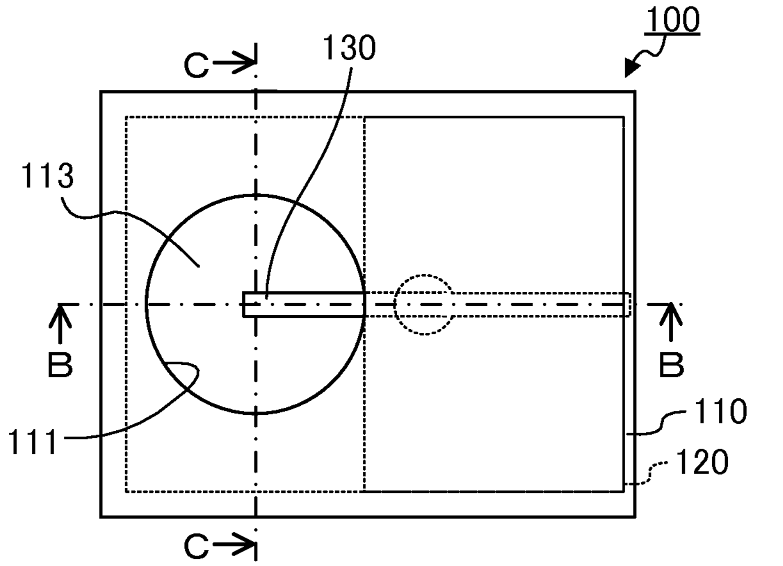
FIGS. 2A to 2C illustrate a configuration of a microchip according to Embodiment 1.
Figure 2B:
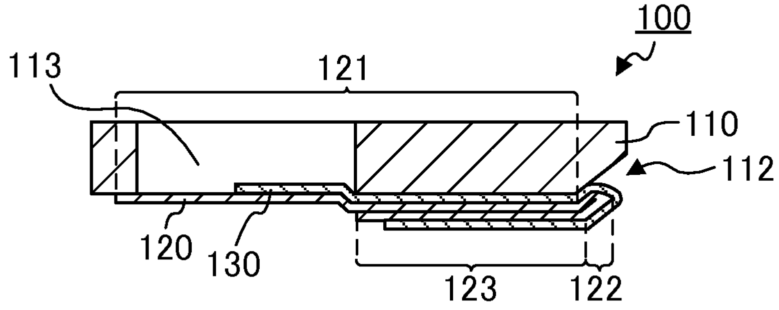
Figure 2C:
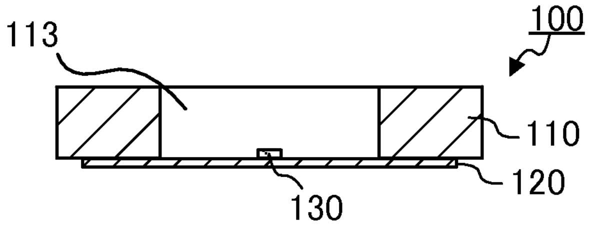
Figure 3A:
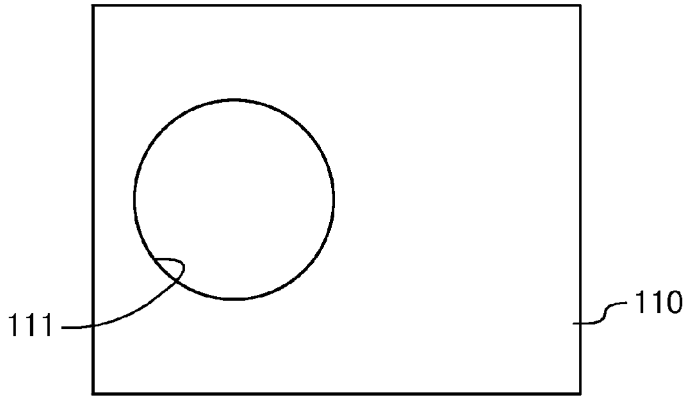
FIG. 3A is a plan view of a substrate.
Figure 3B:
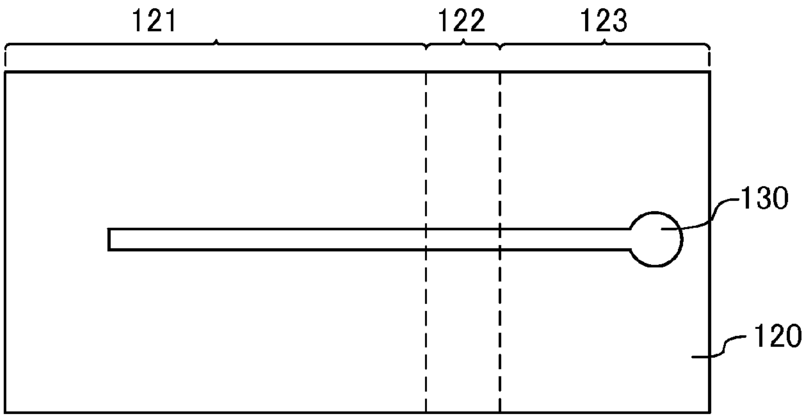
FIG. 3B is a plan view of a film on which a conductive layer is formed.

FIGS. 2A to 3B illustrate a configuration of microchip 100 according to Embodiment 1 of the present invention. FIG. 2A is a plan view of microchip 100, FIG. 2B is a sectional view taken along line B-B of FIG. 2A, and FIG. 2C is a sectional view taken along line C-C of FIG. 2A. FIG. 3A is a plan view of substrate 110, FIG. 3B is a plan view of film 120 on which conductive layer 130 is formed.

As illustrated in FIGS. 2A to 2C, microchip 100 is a plate-shaped device that has housing part 113. Microchip 100 includes substrate 110, film 120 and conductive layer 130. Film 120 includes first region 121, second region 122 and third region 123.

Substrate 110 is a transparent member having a substantially rectangular shape, and includes through hole 111 and cutout part 112. Through hole 111 opens at both surfaces of substrate 110. When one of the openings of through hole 111 is closed with film 120, through hole 111 serves as housing part 113 which can house liquid. The shape and size of through hole 111 are not limited, and can be appropriately set in accordance with the use. For example, through hole 111 has a substantially columnar shape having a diameter of 0.1 to 10 mm.

Cutout part 112 is provided at a position that faces second region 122 of film 120. In the present embodiment, cutout part 112 is provided at an end portion on the rear side of substrate 110. As illustrated in FIG. 2B, second region 122 of film 120 is put in cutout part 112. The shape and size of cutout part 112 are not limited as long as second region 122 of film 120 can be put in cutout part 112. For example, cutout part 112 has a rectangular prism shape. In the present embodiment, cutout part 112 has a substantially triangle pole shape. In addition, for example, the width of cutout part 112 in the longitudinal direction of conductive layer 130 is about 0.5 to 5 mm, and the length of cutout part 112 in the thickness direction of substrate 110 is about 0.5 to 5 mm.

The size and thickness of substrate 110 are not limited, and can be appropriately set in accordance with the use. For example, substrate 110 has a size of 10 mm×20 mm, and a thickness of 1 to 10 mm. The material of substrate 110 is not limited, and any publicly known resin and glass may be appropriately adopted in accordance with the use. Examples of the material of substrate 110 include polyethylene terephthalate, polycarbonate, polymethylmethacrylate, vinyl chloride, polypropylene, polyether, and polyethylene.

Film 120 is a transparent resin film having a substantially rectangular shape. As illustrated in FIG. 3B, film 120 includes first region 121, second region 122 adjacent to first region 121 and third region 123 adjacent to second region 122. As described above, when one of the openings of through hole 111 of substrate 110 is closed with film 120, housing part 113 is formed. First region 121 of film 120 is bonded to one surface (rear side surface) of substrate 110 such that one of the openings of through hole 111 is closed with film 120, and that a part of conductive layer 130 is exposed to the inside of housing part 113. While the method for bonding first region 121 of film 120 to substrate 110 is not limited, film 120 is bonded such that no gap is defined between film 120 and substrate 110 in view of preventing a liquid sample from leaking out when the liquid sample is supplied to housing part 113. For example, film 120 is bonded to substrate 110 by adhesive bonding using an adhesive agent, thermo compression bonding, or the like.

Second region 122 of film 120 is bent such that conductive layer 130 is located on the outside. Second region 122 (bent part) of film 120 is put in cutout part 112. With this structure, the bent part of film 120 can be prevented from protruding in the thickness direction of substrate 110 at the time when microchip 100 is connected to a heater or the like.

Third region 123 of film 120 is bonded to first region 121 of film 120 such that conductive layer 130 is exposed to the exterior. The method for bonding third region 123 of film 120 to first region 121 of film 120 is not limited. For example, third region 123 of film 120 is bonded by using a method similar to the method for bonding first region 121 of film 120 to substrate 110.

The thickness of film 120 is not limited as long as a strength required for housing part 113 is ensured. For example, film 120 has a thickness of about 100 μm.

The material of film 120 is not limited as long as the material has flexibility, and normally, film 120 is made of a resin. Examples of the resin of film 120 include polyethylene terephthalate, polycarbonate, polyolefin, acrylic resin, and cycloolefin polymer (COP) and the like. From the viewpoint of ensuring good adhesion between substrate 110 and film 120, the material of film 120 is preferably identical to that of substrate 110.

As illustrated in FIG. 3B, conductive layer 130 is disposed on one surface of film 120 across first region 121, second region 122 and third region 123, and is capable of conducting electricity or heat. For example, conductive layer 130 is a metal thin film, an electrically conductive ink layer (for example a carbon ink layer) or the like. As illustrated in FIG. 2B, conductive layer 130 disposed on first region 121 of film 120 is disposed on one surface (rear side) of substrate 110 such that a part of conductive layer 130 is exposed to the inside of housing part 113. Conductive layer 130 disposed on second region 122 of film 120 is disposed such that conductive layer 130 is located on the outside of bent film 120. Conductive layer 130 disposed on third region 123 of film 120 is disposed such that conductive layer 130 is exposed to the exterior. Conductive layer 130 may be used as an electrode, an electric heater, a sensor of pH, temperature, flow rate and the like, or an electrochemical detector. In the present embodiment, conductive layer 130 may be used as an electric heater.

The shape and thickness of conductive layer 130 are not limited as long as heat or electricity enough for measurement and processing of a liquid sample and the like can be provided, and can be appropriately set in accordance with the use. For example, conductive layer 130 has a width of about 0.1 to 1 mm, and a thickness of about 10 μm.

(Manufacturing Method of Microchip)

Next, with reference to FIG. 4, a manufacturing method of microchip 100 according to Embodiment 1 will be described. Microchip 100 is manufactured through processes described below.

FIG. 4 is a sectional view illustrating a manufacturing method of microchip 100 according to Embodiment 1. First, as illustrated in FIG. 4A, substrate 110 and film 120 on which conductive layer 130 is formed are prepared. In substrate 110, through hole 111 and cutout part 112 are formed. The method for forming through hole 111 and cutout part 112 in substrate 110 is not limited. For example, through hole 111 and cutout part 112 may be formed by metal molding, lithography or the like. Likewise, the method for forming conductive layer 130 is not limited. Conductive layer 130 may be formed by screen printing of a conductive paste or the like, for example.

Figure 4A:
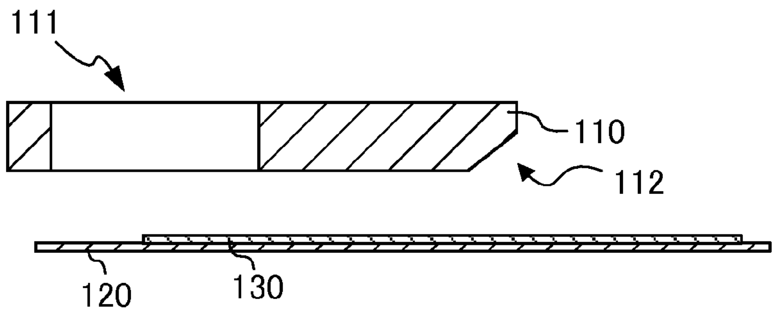
FIGS. 4A to 4D are explanatory sectional views of a manufacturing process of the microchip according to Embodiment 1.
Figure 4B:
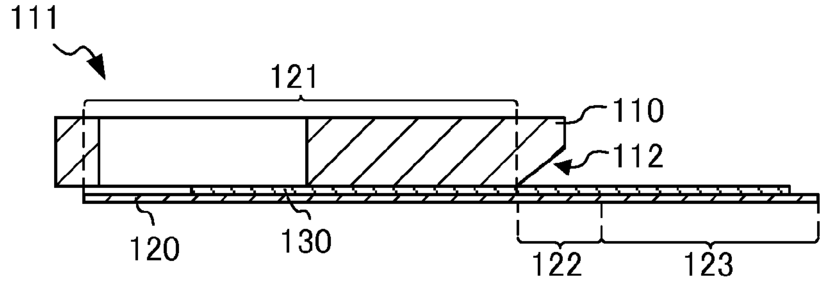
Figure 4C:
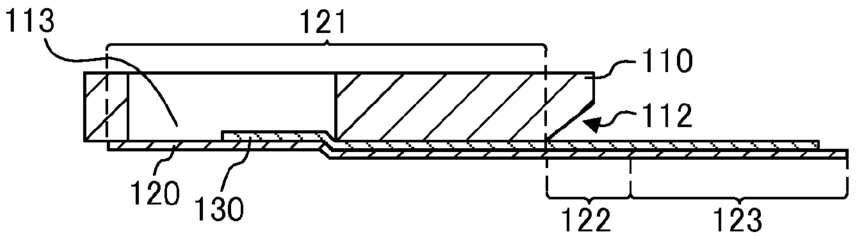
Figure 4D:
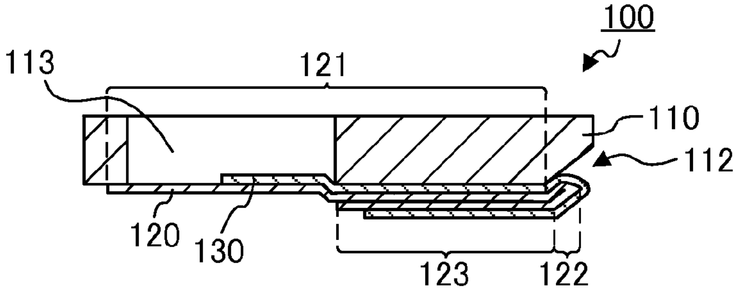

Next, as illustrated in FIG. 4B, first region 121 of film 120 on which conductive layer 130 is formed is disposed on the rear side surface of substrate 110 such that a part of conductive layer 130 is exposed to the inside of through hole 111. Next, as illustrated in FIG. 4C, first region 121 of film 120 is bonded to substrate 110 by thermo compression bonding. In this manner, housing part 113 is formed. Next, as illustrated in FIG. 4D, second region 122 of film 120 is bent such that conductive layer 130 is located on the outside, and third region 123 of film 120 is bonded to first region 121 by thermo compression bonding. At this time, second region 122 (bent part) of film 120 is put in cutout part 112, and does not protrude in the thickness direction of substrate 110. One end of conductive layer 130 is exposed to the inside of housing part 113 on the rear side of substrate 110, and the other end of conductive layer 130 is exposed to the exterior on the rear side of substrate 110. Through the above-mentioned processes, microchip 100 according to the present embodiment can be manufactured.

In microchip 100 manufactured in this manner, third region 123 of film 120 for lining the other end of conductive layer 130 is disposed over substrate 110 with conductive layer 130 and first region 121 of film 120 therebetween. With this structure, as described later, the other end of conductive layer 130 and a heater for heating can be connected together with a sufficient contact pressure.

Conventionally, as a method for exposing one end of a conductive layer to the inside of a housing part while exposing the other end of the conductive layer to the exterior, a method has been known in which conductive layers are formed on both surfaces of a film and the layers are connected together with a through hole line. In comparison with this, in the present invention, while conductive layer 130 is formed on only one surface of film 120, one end of conductive layer 130 is exposed to the inside of housing part 113, and the other end of conductive layer 130 is exposed to the exterior. Therefore, microchip 100 can be manufactured at low cost without using double-sided printing.

(Usage of Microchip)

Next, with reference to FIG. 5, usage of microchip 100 according to Embodiment 1 will be described.

Figure 1A:
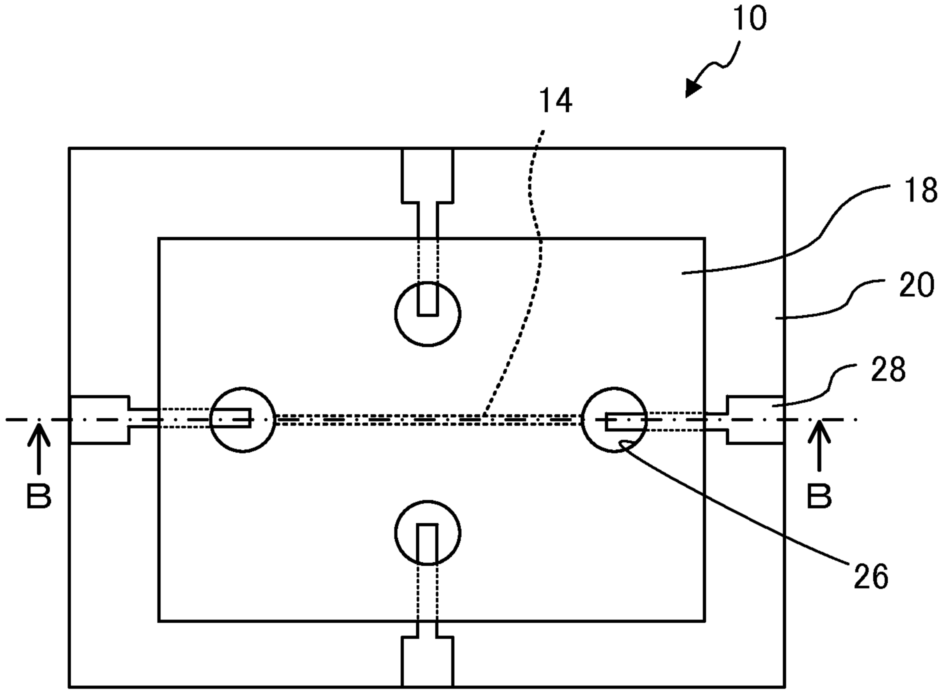
FIGS. 1A and 1B illustrate a configuration of a microchannel chip disclosed in PTL 1.
Figure 1B:
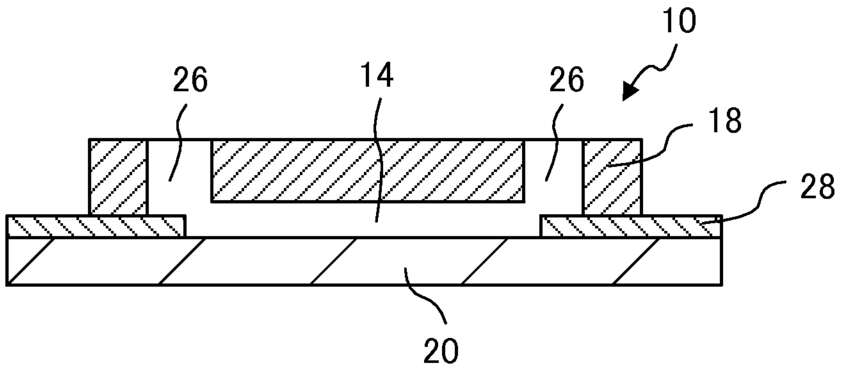
Figure 5:
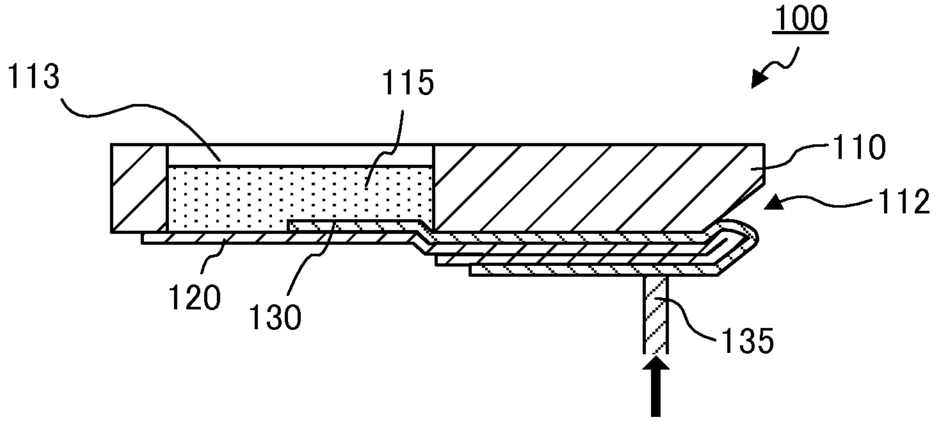
FIG. 5 is an explanatory view of a mode of using the microchip according to Embodiment 1.

FIG. 5 illustrates a mode of using microchip 100 according to Embodiment 1. As illustrated in FIG. 5, liquid 115 such as reagent and a liquid sample is provided in housing part 113 of microchip 100. Heater 135 is pressed against conductive layer 130. Since conductive layer 130 is disposed over substrate 110 with film 120 and conductive layer 130 therebetween, heater 135 can be connected with a sufficient contact pressure. In addition, since conductive layer 130 and heater 135 can be connected on the inside relative to the external edge of substrate 110 in the above-mentioned manner, microchip 100 can be downsized (see and compare FIG. 1B and FIG. 5). Further, when the heater 135 is heated in this state, the liquid 115 in housing part 113 can be heated through conductive layer 130.

(Effect)

As described above, in microchip 100 according to Embodiment 1, film 120 is bent to expose one end of conductive layer 130 to the inside of housing part 113 and to expose the other end of conductive layer 130 to the exterior. Conductive layer 130 and heater 135 can stably make contact with each other on substrate 110. Thus, conductive layer 130 and heater 135 can be connected together with a sufficient contact pressure. Other than the heater, microchip 100 according to Embodiment 1 can be appropriately disposed to, for example, a measurement device having an insertion-type connector and the like, whereby measurement, processing and the like of a trace substance can be correctly performed.

While conductive layer 130 is used as a heater for heat treatment in the present embodiment, the use of the conductive layer is not limited to a heater for heat treatment.

Figure 6:
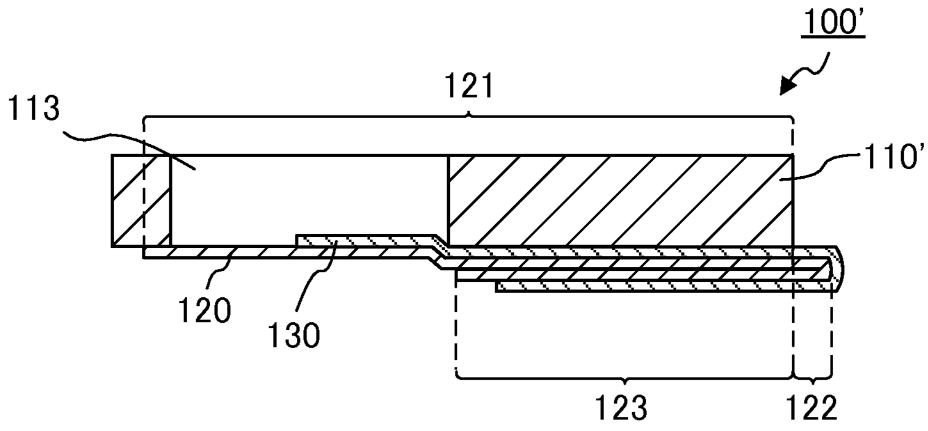
FIG. 6 is a sectional view of a microchip according to a modification of Embodiment 1.

In addition, the shape of the substrate is not limited to the shape illustrated in FIG. 3A and FIG. 4A. FIG. 6 is a sectional view of microchip 100' according to a modification of Embodiment 1. While substrate 110 having cutout part 112 is adopted in microchip 100 in Embodiment 1, substrate 110' having no cutout part 112 may also be adopted as illustrated in FIG. 6. In this case, second region 122 of film 120 is bent such that conductive layer 130 is located outside. At this time, from the viewpoint of preventing second region 122 of film 120 from protruding in the thickness direction of substrate 110', it is preferable that second region 122 of film 120 be disposed on the outside relative to the external edge of substrate 110'.

Figure 7A:
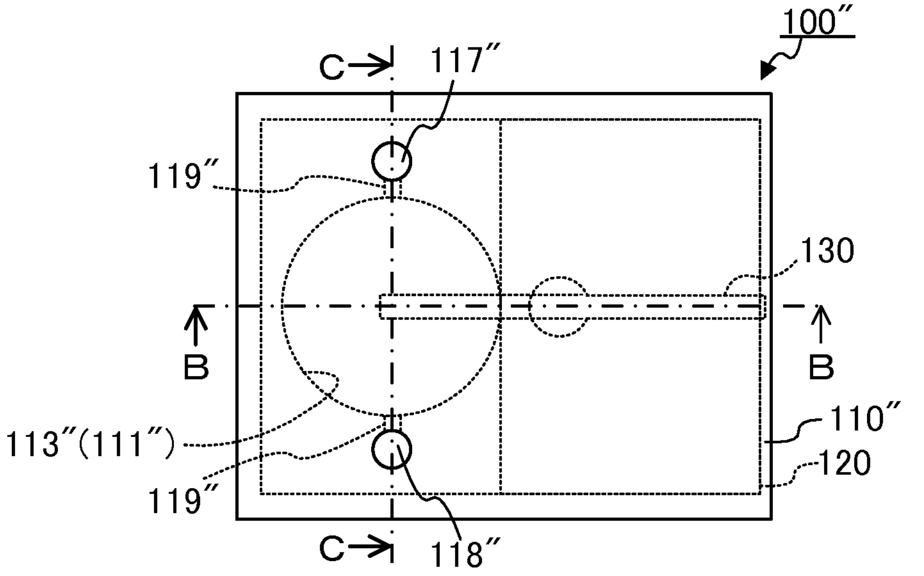
FIGS. 7A to 7C illustrate a configuration of a microchip according to a modification of Embodiment 1.

In addition, in the present embodiment, microchip 100 has housing part 113 that is formed by closing the opening of through hole 111 of substrate 110 with film 120. Alternatively, substrate 110 may has a recess that serves as housing part 113 in place of through hole 111. FIG. 7A is a plan view of microchip 100" according to a modification of Embodiment 1, FIG. 7B is a sectional view taken along line B-B of FIG. 7A, and FIG. 7C is a sectional view taken along line C-C of FIG. 7A.

Figure 7B:
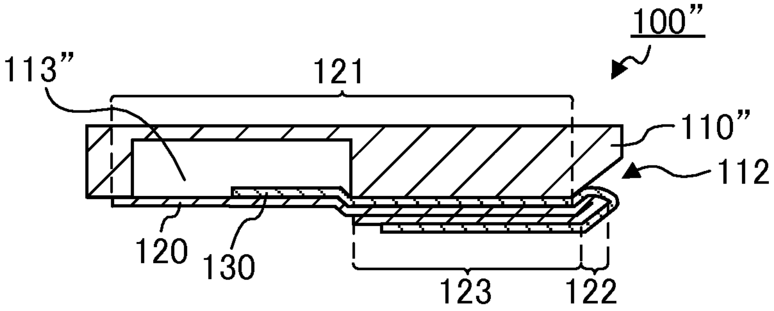
Figure 7C:
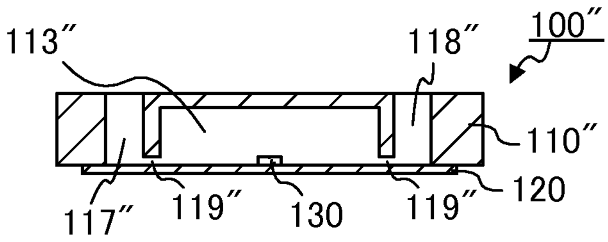

As illustrated in FIGS. 7A to 7C, substrate 110" has recess 111" in place of through hole 111. The opening of recess 111" is closed with first region 121 of film 120 and thus housing part 113" that can house liquid is formed. In addition, substrate 110" further includes two second through holes and two grooves. Openings of the two second through holes are closed with first region 121 of film 120 to form outlet 118" and inlet 117" for introducing liquid to housing part 113". In addition, openings of the two grooves are closed with first region 121 of film 120 to form channel 119" through which liquid flows. One end of each of two channels 119" is in communication with housing part 113", and the other end of each of two channels 119" is in communication with inlet 117" or outlet 118". With this structure, liquid can be introduced from the exterior to housing part 113".

Embodiment 2

In Embodiment 2, microchannel chip 200 that has channel 217 through which liquid can move by capillarity, and that can apply a voltage to reagent, a liquid sample, and the like will be described.

Microchannel chip 200 according to Embodiment 2 is different from microchip 100 according to Embodiment 1 in substrate 210 and conductive layer 230. Therefore, the same components as those of microchip 100 according to Embodiment 1 are denoted with the same reference numerals and their descriptions are omitted, and components different from substrate 110 and conductive layer 130 of microchip 100 are mainly described.

(Configuration of Microchannel Chip)

Figure 8A:
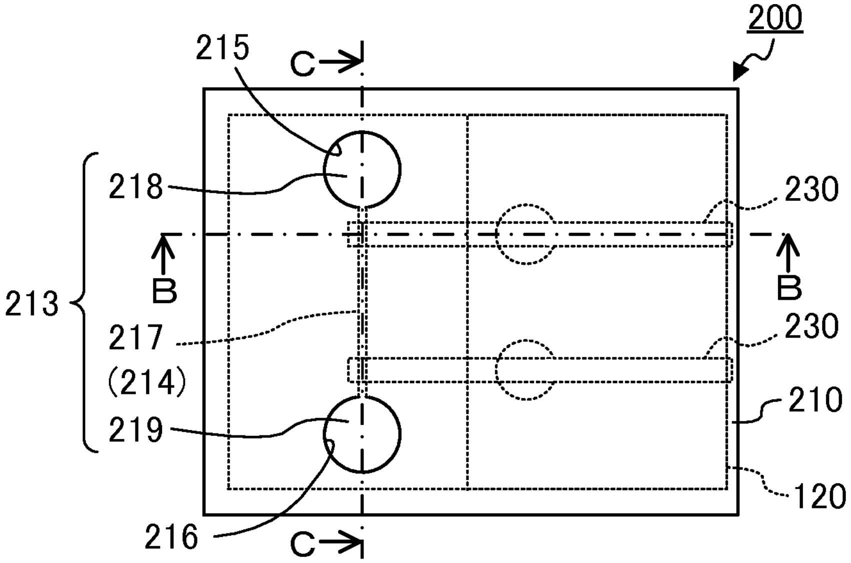
FIGS. 8A to 8C illustrate a configuration of a microchannel chip according to Embodiment 2.
Figure 8B:
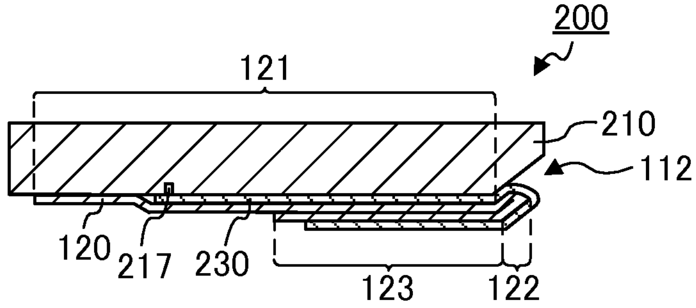
Figure 8C:
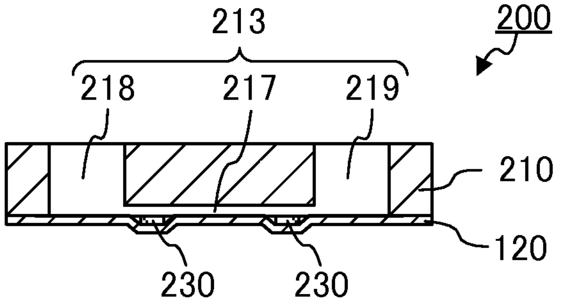

FIGS. 8A to 8C illustrate a configuration of microchannel chip 200 according to Embodiment 2. FIG. 8A is a plan view of microchannel chip 200, FIG. 8B is a sectional view taken along line B-B of FIG. 8A, and FIG. 8C is a sectional view taken along line C-C of FIG. 8A.

As illustrated in FIGS. 8A to 8C, microchannel chip 200 includes substrate 210, film 120 and two conductive layers 230.

Substrate 210 is a transparent member having a substantially rectangular shape. Substrate 210 includes groove 214, third through hole 215, fourth through hole 216 and cutout part 112. Groove 214 opens at one surface (rear surface) of substrate 210. When the opening of groove 214 is closed with film 120, channel 217 through which liquid flows is formed. The cross-sectional shape of groove 214 in a direction orthogonal to its flow direction is not limited, and for example, the cross-sectional shape of groove 214 is a substantially rectangular shape with each side (width and depth) having a length of several tens of micrometers.

Third through hole 215 and fourth through hole 216 each open at both surfaces of substrate 210. Third through hole 215 is in communication with an end portion of groove 214. In addition, fourth through hole 216 is in communication with the other end portion of groove 214. The shapes of third through hole 215 and fourth through hole 216 are not limited, and for example, third through hole 215 and fourth through hole 216 each have a substantially columnar shape. Third through hole 215 and fourth through hole 216 may have the same size or different sizes. The diameters of third through hole 215 and fourth through hole 216 are not limited, and for example, third through hole 215 and fourth through hole 216 each have a diameter of about 0.1 to 3 mm. The shape and size of cutout part 112 are the same as those of Embodiment 1, and therefore the descriptions thereof will be omitted.

The size, thickness and material of substrate 210 are the same as those of substrate 110 according to Embodiment 1, and therefore the descriptions thereof will be omitted.

In Embodiment 2, the openings of groove 214, third through hole 215 and fourth through hole 216 of substrate 210 are closed with film 120 to form housing part 213 including channel 217, first recess 218 and second recess 219. To be more specific, the opening of groove 214 is closed with film 120 to form channel 217 through which liquid can move by capillarity. In addition, openings of third through hole 215 and fourth through hole 216 of substrate 210 on the side of the opening of groove 214 are closed to form first recess 218 and second recess 219. First recess 218 and second recess 219 are in communication with each other via channel 217.

As illustrated in FIGS. 8A to 8C, two conductive layers 230 are disposed on one surface of film 120 across first region 121, second region 122 and third region 123, and are capable of conducting electricity or heat. Conductive layers 230 disposed on first region 121 of film 120 are each disposed on one surface (rear side) of substrate 210 such that conductive layers 230 are partly exposed to the inside of channel 217. Conductive layer 230 disposed on second region 122 of film 120 is disposed such that it is located on the outside of bent film 120. Conductive layer 230 disposed on third region 123 of film 120 is disposed such that it is exposed to the exterior. The material, thickness, usage and the like of conductive layer 230 are the same as those of Embodiment 1, and therefore the descriptions thereof will be omitted.

In microchannel chip 200 according to Embodiment 2, conductive layer 230 is connected to an external power source through an electrode connector not illustrated. By applying a voltage between two conductive layers 230 in the state where a liquid sample exists in channel 217, a voltage can be applied to the liquid sample in channel 217. In addition, also in Embodiment 2, conductive layer 230 is disposed over substrate 210 with film 120 and conductive layer 230 therebetween, and thus an electrode connector can be connected with a sufficient contact pressure. In addition, since conductive layer 230 and the electrode connector can be connected together on the inside relative to the external edge of substrate 210, microchannel chip 200 can be downsized.

(Effect)

As described above, in microchannel chip 200 according to Embodiment 2, film 120 is bent to expose one end of conductive layer 230 to the inside of channel 217, and to expose the other end of conductive layer 230 to the exterior. Conductive layer 230 and the electrode connector can stably make contact with each other on substrate 210. Thus, conductive layer 230 and the electrode connector can be connected together with a sufficient contact pressure. Microchannel chip 200 according to Embodiment 2 can be appropriately disposed to, for example, a measurement device having an insertion-type connector and the like, whereby measurement, processing and the like of a trace substance can be correctly performed.

While conductive layer 230 is used as an electrode for applying a voltage in microchannel chip 200 according to Embodiment 2, the usage of conductive layer is not limited to an electrode for applying a voltage.

In addition, while microchip 100 and microchannel chip 200 are used for processing, analyzing and the like of a liquid sample in Embodiment 1 and Embodiment 2, the fluid handling device according to the embodiments of the present invention may be used for processing, analyzing, and the like of fluid (for example, mixture, slurry, suspension liquid or the like), other than liquid.

INDUSTRIAL APPLICABILITY

The fluid handling device of the embodiments of the present invention is suitable for, for example, a microchip or a microchannel chip that are used for analyzing a trace substance in the scientific field, the medical field, and the like.

REFERENCE SIGNS LIST

10 Microchannel chip
14 Micro channel (channel)
18 Substrate
20 Plate
26 Reservoir
28 Electrically conductive layer
100, 100', 100", 200 Micro (channel) chip
110, 110', 110", 210 Substrate
111 Through hole
111" Recess
112 Cutout part
113, 113", 213 Housing part
115 Liquid
117" Inlet
118" Outlet
119" Channel
120 Film
121 First region
122 Second region
123 Third region

130, 230 Conductive layer
135 Heater
214 Groove
215 Third through hole
216 Fourth through hole
217 Channel
218 First recess
219 Second recess

The invention claimed is:

1. A fluid handling device comprising:

a substrate including a through hole or a recess;

a film including a first region, a second region adjacent to the first region and a third region adjacent to the second region; and a conductive layer disposed on one surface of the film across the first region, the second region and the third region, the conductive layer being configured to conduct electricity or heat, wherein the first region of the film is bonded to one surface of the substrate such that one of openings of the through hole or an opening of the recess is closed to form a housing part for housing liquid, and that a part of the conductive layer is exposed to an inside of the housing part, the second region of the film is bent such that the conductive layer is located on an outside, and the third region of the film is bonded to the first region of the film such that the conductive layer is exposed to an exterior.

2. The fluid handling device according to claim 1, wherein the substrate includes a cutout part at a position facing the second region of the film.

3. The fluid handling device according to claim 1, wherein the housing part includes a channel through which liquid moves by capillarity.

4. The fluid handling device according to claim 2, wherein the housing part includes a channel through which liquid moves by capillarity.

5. The fluid handling device according to claim 1, wherein the conductive layer is a metal thin film or a conductive ink layer.

6. The fluid handling device according to claim 2, wherein the conductive layer is a metal thin film or a conductive ink layer.

7. The fluid handling device according to claim 3, wherein the conductive layer is a metal thin film or a conductive ink layer.

8. The fluid handling device according to claim 4, wherein the conductive layer is a metal thin film or a conductive ink layer.

* * * * *